(12) United States Patent
Kerr et al.

(10) Patent No.: US 9,717,549 B2
(45) Date of Patent: Aug. 1, 2017

(54) SURGICAL FORCEPS

(71) Applicant: COVIDIEN LP, Mansfield, MA (US)

(72) Inventors: Duane E. Kerr, Loveland, CO (US); James D. Allen, IV, Broomfield, CO (US); Edward M. Chojin, Boulder, CO (US); Allan J. Evans, Golden, CO (US); Russell D. Hempstead, Lafayette, CO (US); Glenn A. Horner, Boulder, CO (US); Mark J. Huseman, Broomfield, CO (US); Daniel A. Joseph, Golden, CO (US); Arlen J. Reschke, Longmont, CO (US); Robert M. Sharp, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 339 days.

(21) Appl. No.: 14/513,732

(22) Filed: Oct. 14, 2014

(65) Prior Publication Data

US 2015/0066076 A1    Mar. 5, 2015

Related U.S. Application Data

(63) Continuation of application No. 13/251,380, filed on Oct. 3, 2011, now Pat. No. 8,864,795.

(51) Int. Cl.
*A61B 18/14*    (2006.01)
*A61B 17/295*    (2006.01)
(Continued)

(52) U.S. Cl.
CPC ........ *A61B 18/1445* (2013.01); *A61B 17/282* (2013.01); *A61B 17/295* (2013.01);
(Continued)

(58) Field of Classification Search
CPC . A61B 17/28; A61B 18/1442; A61B 18/1447; A61B 17/282; A61B 17/295;
(Continued)

(56) References Cited

U.S. PATENT DOCUMENTS

D249,549 S    9/1978 Pike
D263,020 S    2/1982 Rau, III
(Continued)

FOREIGN PATENT DOCUMENTS

CN    201299462        9/2009
DE    2415263 A1    10/1975
(Continued)

OTHER PUBLICATIONS

Int'l Search Report EP 10 185405.7 dated Jan. 5, 2011.
(Continued)

*Primary Examiner* — Thomas McEvoy

(57) ABSTRACT

A forceps includes an end effector assembly having first and second jaw members movable between a spaced-apart position and an approximated position for grasping tissue therebetween. A knife assembly having a cutting blade disposed at a distal end thereof is also provided. The knife assembly is translatable relative to the end effector assembly between a retracted position and an extended position, wherein the cutting blade extends between the jaw members to cut tissue grasped therebetween. The knife assembly includes a proximal component and a first distal component that includes the cutting blade. The proximal and first distal components are removably coupled to one another to facilitate replacement of the first distal component while the end effector assembly remains in a substantially assembled condition, i.e., without requiring substantial disassembly of the end effector assembly.

11 Claims, 11 Drawing Sheets

(51) Int. Cl.
  *A61B 18/08*    (2006.01)
  *A61B 17/28*    (2006.01)
  *A61B 17/3213*  (2006.01)
  *A61B 17/29*    (2006.01)
  *A61B 18/18*    (2006.01)
  *A61B 18/00*    (2006.01)
  *A61B 17/00*    (2006.01)

(52) U.S. Cl.
  CPC ........ *A61B 18/085* (2013.01); *A61B 18/1442* (2013.01); *A61B 17/3213* (2013.01); *A61B 18/18* (2013.01); *A61B 2017/0023* (2013.01); *A61B 2017/00473* (2013.01); *A61B 2017/2933* (2013.01); *A61B 2017/2937* (2013.01); *A61B 2017/2939* (2013.01); *A61B 2017/2946* (2013.01); *A61B 2018/0063* (2013.01); *A61B 2018/0097* (2013.01); *A61B 2018/00345* (2013.01); *A61B 2018/00404* (2013.01); *A61B 2018/00589* (2013.01); *A61B 2018/00595* (2013.01); *A61B 2018/1452* (2013.01); *A61B 2018/1455* (2013.01); *A61B 2018/1462* (2013.01); *Y10T 29/49815* (2015.01)

(58) Field of Classification Search
  CPC .... A61B 2017/2933; A61B 2017/2937; A61B 2017/305; A61B 18/1445
  See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| 4,763,669 A | 8/1988 | Jaeger |
| D298,353 S | 11/1988 | Manno |
| D299,413 S | 1/1989 | DeCarolis |
| 5,258,001 A | 11/1993 | Corman |
| D343,453 S | 1/1994 | Noda |
| D348,930 S | 7/1994 | Olson |
| D349,341 S | 8/1994 | Lichtman et al. |
| 5,344,424 A | 9/1994 | Roberts et al. |
| D354,564 S | 1/1995 | Medema |
| D358,887 S | 5/1995 | Feinberg |
| 5,540,685 A | 7/1996 | Parins et al. |
| 5,611,808 A | 3/1997 | Hossain et al. |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| 5,913,874 A | 6/1999 | Berns et al. |
| 5,960,544 A | 10/1999 | Beyers |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,366,709 B2 | 2/2013 | Schechter et al. |
| 8,425,504 B2 | 4/2013 | Orton et al. |
| 8,469,716 B2 | 6/2013 | Fedotov et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,663,222 B2 | 3/2014 | Anderson et al. |
| 8,679,098 B2 | 3/2014 | Hart |
| 8,685,009 B2 | 4/2014 | Chernov et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,898,888 B2 | 12/2014 | Brandt et al. |
| 8,900,232 B2 | 12/2014 | Ourada |
| 8,906,018 B2 | 12/2014 | Rooks et al. |
| 2010/0179545 A1 | 7/2010 | Twomey et al. |
| 2010/0179547 A1* | 7/2010 | Cunningham ...... A61B 18/1445 606/51 |
| 2011/0238065 A1* | 9/2011 | Hunt .................... A61B 17/295 606/45 |
| 2012/0083785 A1 | 4/2012 | Artale et al. |
| 2012/0083786 A1 | 4/2012 | Roy et al. |
| 2012/0083827 A1 | 4/2012 | Artale et al. |
| 2012/0123404 A1 | 5/2012 | Craig |
| 2012/0123410 A1 | 5/2012 | Craig |
| 2012/0123413 A1 | 5/2012 | Chernov et al. |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172924 A1 | 7/2012 | Allen, IV |
| 2012/0184988 A1 | 7/2012 | Twomey |
| 2012/0184989 A1 | 7/2012 | Twomey |
| 2012/0209263 A1 | 8/2012 | Sharp et al. |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |

(56) References Cited

U.S. PATENT DOCUMENTS

| | | |
|---|---|---|
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1 | 1/2013 | Sims et al. |
| 2013/0022495 A1 | 1/2013 | Allen, IV et al. |
| 2013/0041370 A1 | 2/2013 | Unger |
| 2013/0046295 A1 | 2/2013 | Kerr et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |
| 2013/0178852 A1 | 7/2013 | Allen, IV et al. |
| 2013/0185922 A1 | 7/2013 | Twomey et al. |
| 2013/0190753 A1 | 7/2013 | Garrison et al. |
| 2013/0190760 A1 | 7/2013 | Allen, IV et al. |
| 2013/0197503 A1 | 8/2013 | Orszulak |
| 2013/0226178 A1 | 8/2013 | Brandt et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 10045375 C2 | 10/2002 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1 159 926 A2 | 12/2001 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 20013400 | 11/2001 |
| JP | 2002-528166 A | 9/2002 |
| JP | 2003245285 A | 9/2003 |
| JP | 2004-517668 A | 6/2004 |
| JP | 2004-528869 A | 9/2004 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 2005/110264 A2 | 11/2005 |

OTHER PUBLICATIONS

Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.

(56) References Cited

OTHER PUBLICATIONS

Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/085,144, filed Apr. 12, 2011, Keir Hart.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.

Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.

(56) References Cited

OTHER PUBLICATIONS

Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report Ep 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Intl Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.

* cited by examiner

SURGICAL FORCEPS

This application is a continuation application of U.S. patent application Ser. No. 13/251,380, filed on Oct. 3, 2011, the entire contents of which are hereby incorporated herein by reference.

BACKGROUND

Background

The present disclosure relates to surgical instruments and, more particularly, to surgical instruments having replaceable components and/or a reduced number of components to facilitate cleaning, sterilization and replacement of disposable components in preparation for reuse.

Technical Field

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

Generally, surgical instruments, including forceps, can be classified as single-use instruments, e.g., instruments that are discarded after a single use, partially-reusable instruments, e.g., instruments including both disposable portions and portions that are sterilizable for reuse, and completely reusable instruments, e.g., instruments that are completely sterilizable for repeated use. As can be appreciated, those instruments (or components of instruments) that can be sterilized and reused help reduce the costs associated with the particular surgical procedure for which they are used. However, although reusable surgical instruments are cost-effective, it is important that these instruments be capable of performing the same functions as their disposable counterparts, that any disposable components of these instruments be efficiently removable and replaceable with new components, and that the reusable components be efficiently and satisfactorily sterilizable for reuse.

SUMMARY

As used herein, the term "distal" refers to the portion that is being described which is further from a user, while the term "proximal" refers to the portion that is being described which is closer to a user.

In accordance with one aspect of the present disclosure, a forceps is provided. The forceps includes an end effector assembly having first and second jaw members. One or both of the jaw members is movable relative to the other between a spaced-apart position and an approximated position for grasping tissue therebetween. The forceps also includes a knife assembly having a cutting blade disposed at a distal end thereof. The knife assembly is translatable relative to the end effector assembly between a retracted position and an extended position, wherein the cutting blade extends between the jaw members to cut tissue grasped therebetween. The knife assembly includes a proximal component and a first distal component that includes the cutting blade. The proximal and first distal components are removably coupled to one another to facilitate replacement of the first distal component while the end effector assembly remains in a substantially assembled condition.

In one aspect, the proximal and first distal components are coupled to one another by one or more pin-aperture engagements.

In another aspect, one of the proximal and first distal components includes one or more cantilever springs having a tab extending from a free end thereof. The tab(s) is configured to engage a complementary notch defined within the other component to removably couple the proximal and first distal components to one another.

In another aspect, a releasable locking mechanism is included. The releasable locking mechanism is movable between a locked position, wherein the proximal and first distal components are secured to one another, and an unlocked position, wherein the proximal and first distal components are removable from one another. In the unlocked position, for example, the first distal component may be replaceable with a second distal component.

In still another aspect, the end effector assembly includes a window defined therethrough that is configured to provide access to a connection area between the proximal and distal components. As such, the window permits coupling and decoupling of the proximal and first distal components to one another.

In yet another aspect, the proximal and first distal components are formed as a single monolithic piece. In such an aspect, in order to decouple the components, the single piece is broken into proximal and first distal components. The broken proximal component may then be engaged with a second distal component, e.g., via welding.

In still yet another aspect, the jaw members are pivotably coupled to one another about a pivot pin and the first distal component includes an elongated slot having an open proximal end. The elongated slot is configured to permit passage of the pivot pin therethrough from the open proximal end thereof to facilitate decoupling of the proximal and first distal components from one another. A second distal component may also be is provided. The second distal component is similar to the first distal component and is configured to replace the first distal component. More specifically, the second distal component includes an elongated slot having an open proximal end that is configured to permit passage of the pivot pin therethrough from the open proximal end thereof to facilitate coupling of the proximal and second distal components to one another.

A method of manufacturing a forceps is also provided in accordance with the present disclosure. The method includes providing a forceps including an end effector assembly having first and second jaw members movable between a spaced-apart position and an approximated position for grasping tissue therebetween. The forceps further includes a knife assembly translatable relative to the end effector assembly from a retracted position to an extended position for cutting tissue grasped between the jaw members. The knife assembly has a proximal component and a first distal component including a cutting blade disposed at a distal end thereof. The method further includes coupling the proximal component and the first distal component to one another, decoupling the proximal component and the first distal component from one another while the end effector assembly remains in a substantially assembled condition, and coupling a second distal component having a cutting blade disposed at a distal end thereof with the proximal component while the end effector assembly remains in a substantially assembled condition.

In some aspects, the proximal and first distal components and/or the proximal and second distal components are coupled to one another according to any of the configurations described above.

Additionally or alternatively, the knife assembly further includes a releasable locking mechanism. In such an aspect, the method may further include transitioning the releasable locking mechanism from a locked position, wherein the proximal and first distal components are secured to one another, to an unlocked position for decoupling the proximal and first distal components, replacing the first distal component with a second distal component, and transitioning the releasable locking mechanism from the unlocked position back to the locked position to couple the proximal component and second distal component to one another.

In yet another aspect, the end effector assembly further includes a window defined therethrough. In such an aspect, the method may further include decoupling the first distal component from the proximal component through the window, and coupling the second distal component to the proximal component through the window.

In still yet another aspect, the proximal and first distal components are decoupled from one another via breaking the knife assembly into proximal and first distal components. Thereafter, the first distal component may be replaced with a second distal component that is coupled to the proximal component, e.g., via welding.

Any or all of the aspects described herein, to the extent consistent with one another, may be used in conjunction with any or all of the other aspects of the present disclosure.

BRIEF DESCRIPTION OF THE DRAWINGS

Various aspects of the subject instrument are described herein with reference to the drawings wherein like reference numerals identify similar or identical elements.

DETAILED DESCRIPTION

Figure 1:
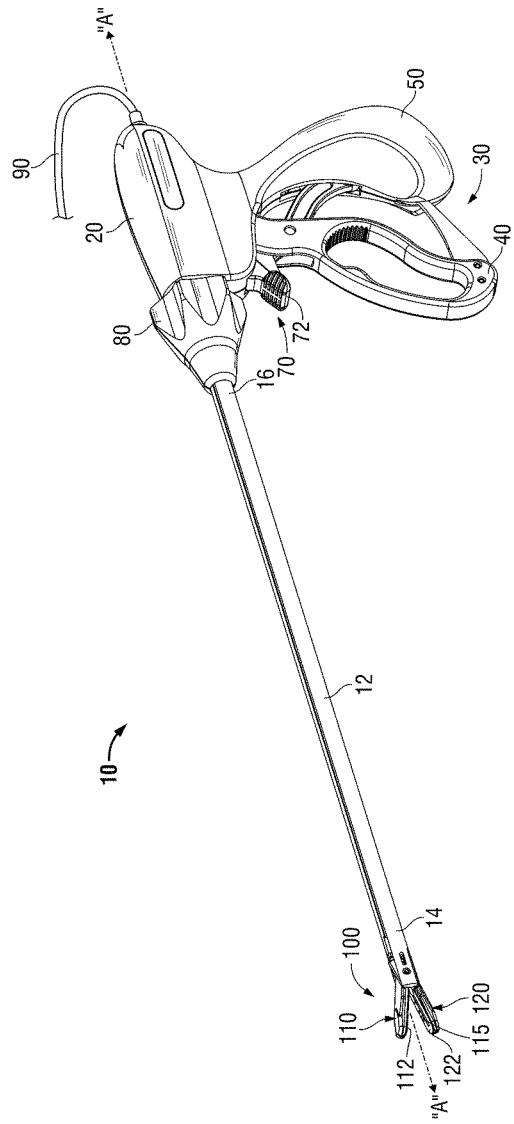
FIG. 1 is a front, perspective view of a forceps provided in accordance with the present disclosure.

Referring now to FIG. 1, a forceps 10 for use in connection with endoscopic surgical procedures is shown, although forceps 10 may also be configured for use in connection with traditional open surgical procedures. Forceps 10 defines a longitudinal axis "A-A" and includes a housing 20, a handle assembly 30, a trigger assembly 70, a rotating assembly 80 and an end effector assembly 100. End effector assembly 100 includes first and second jaw members 110, 120, respectively, configured to pivot relative to one another between a spaced-apart position and an approximated position for grasping tissue therebetween. Forceps 10 further includes a shaft 12 having a distal end 14 configured to mechanically engage end effector assembly 100 and a proximal end 16 that mechanically engages housing 20.

Forceps 10 also includes a cable 90 that connects forceps 10 to a generator (not shown) or other suitable energy source, although forceps 10 may alternatively be configured as a battery powered instrument. Cable 90 includes a wire (or wires) (not explicitly shown) extending therethrough, into housing 20, and through shaft 12 to ultimately connect the source of energy (not explicitly shown) to jaw member 110 and/or jaw member 120 of end effector assembly 100. However, any other suitable connection(s) for supplying energy to jaw member 110 and/or jaw member 120 may also be provided.

With continued reference to FIG. 1, handle assembly 30 includes a fixed handle 50 and a movable handle 40. Fixed handle 50 is integrally associated with housing 20 and handle 40 is movable relative to fixed handle 50. Rotating assembly 80 is rotatable in either direction about a longitudinal axis "A-A" to rotate end effector 100 about longitudinal axis "A-A." The housing 20 contains the internal working components of the forceps 10.

End effector assembly 100 is attached at distal end 14 of shaft 12 and includes opposing jaw members 110 and 120. End effector assembly 100 is designed as a bilateral assembly, i.e., where both jaw members 110 and 120 are movable relative to one another and relative to shaft 12. However, end effector assembly 100 may alternatively be configured as a unilateral assembly, i.e., where one of the jaw members 110, 120 is fixed relative to shaft 12 and the other jaw member 110, 120 is movable between the spaced-apart and approximated positions.

As shown in FIG. 1, each jaw member 110, 120 includes an electrically conductive tissue sealing plate 112, 122 disposed thereon. Tissue sealing plates 112, 122 are positioned on jaw members 110, 120, respectively, to define opposed tissue sealing surfaces for grasping and sealing tissue between jaw members 110, 120. In some embodiments, a knife assembly is disposed within shaft 12 and a knife channel 115 is defined within one or both of tissue sealing plates 112, 122, of jaw members 110, 120, respectively, to permit reciprocation of a knife blade therethrough for cutting tissue grasped between jaw members 110, 120. In such an embodiment, trigger 72 of trigger assembly 70 is operable to advance the knife blade between a retracted position and an extended position to cut tissue grasped between jaw members 110, 120.

Continuing with reference to FIG. 1, movable handle 40 of handle assembly 30 is ultimately connected to a drive assembly (not shown) that, together, mechanically cooperate to impart movement of jaw members 110 and 120 between the spaced-apart position and the approximated position to grasp tissue between sealing plates 112 and 122 of jaw members 110, 120, respectively. As shown in FIG. 1, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120.

Various end effector assemblies configured for use with forceps 10, along with various other embodiments of surgical forceps are described in detail hereinbelow. Various embodiments of knife assemblies provided in accordance with the present disclosure and configured for use with forceps 10 or any other suitable surgical instrument will also be described in greater detail below. In each of these embodiments, as will become apparent in view of the following, the forceps, end effector assemblies, knife assemblies, and/or specific components thereof are configured to facilitate the replacement of any disposable components and/or the cleaning and sterilization of any reusable components in preparation for reuse. In particular, each of the embodiments detailed below helps reduce the costs associated with preparing the forceps or components thereof for reuse and/or improves the efficiency of preparing the forceps or components thereof for reuse. Further, to the extent they are consistent with one another, it is envisioned that the features of any of the embodiments below may be similarly used in conjunction with any of the other embodiments.

Figure 2A:
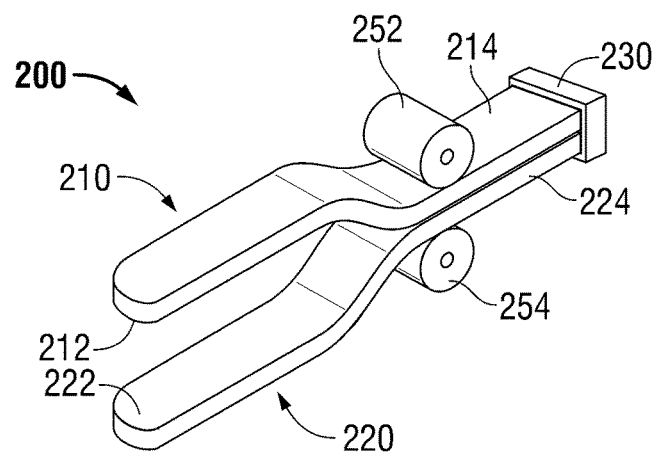
FIG. 2A is a perspective view of an end effector assembly configured for use with the forceps of FIG. 1.
Figure 2B:
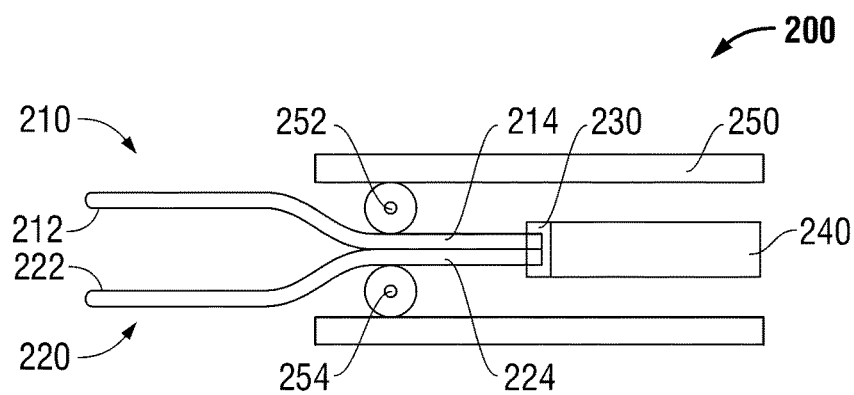
FIG. 2B is a longitudinal, cross-sectional view of the end effector assembly of FIG. 2A shown engaged to a shaft of the forceps of FIG. 1.

Referring now to FIGS. 2A-2B, in conjunction with FIG. 1, an end effector assembly configured for use with forceps 10 is shown generally identified by reference numeral 200. End effector assembly 200 includes first and second jaw members 210, 220, respectively. Each jaw member 210, 220 includes a respective proximal support arm 214, 224 that is formed at least partially from a flexible material and a distal portion defining an opposed electrically-conductive tissue sealing surface 212, 222, respectively. Proximal support arms 214, 224 are coupled to one another at the proximal ends thereof via a base member 230. Base member 230, in turn, is coupled to rod 240 to maintain jaw members 210, 220 in fixed longitudinal position. Base member 230 may be removably coupled to rod 240 such that end effector assembly 200 may be removed and replaced with a new end effector assembly 200 (or the original end effector assembly, once properly cleaned) simply by disengaging base member 230 from rod 240 and engaging the new base member with rod 240.

As best shown in FIG. 2B, proximal support arms 214, 224 of jaw members 210, 220, respectively, are disposed within an inner tube 250. Inner tube 250 is disposed within shaft 12 (see FIG. 1) and is longitudinally translatable relative to shaft 12 (FIG. 1) and jaw members 210, 220. Inner tube 250 includes a pair of opposed rollers 252, 254 rotatably engaged therein on opposite sides of proximal support arms 214, 224, respectively, such that, as inner tube 250 is translated relative to jaw members 210, 220, rollers 252, 254 are rolled along the outer surfaces of proximal support arms 214, 224, respectively.

With continued reference to FIGS. 2A-2B, in use, end effector assembly 200 is positioned such that tissue to be grasped and treated is disposed between jaw members 210, 220. Next, inner tube 250 is translated distally relative to jaw members 210, 220, e.g., via depressing movable handle 40 (FIG. 1), such that rollers 252, 254 are advanced distally along proximal support arms 214, 224, respectively. As can be appreciated, due to the at least partially flexible configuration of support arms 214, 224, jaw members 210, 220 are moved toward one another to grasp tissue disposed therebetween as rollers 252, 254 are advanced distally along proximal support arms 214, 224, respectively. Energy may then be supplied to either or both of sealing surfaces 212, 222 of jaw members 210, 220, respectively, to treat, e.g., seal, tissue grasped therebetween. In order to release tissue from between jaw members 210, 220, inner tube 250 is translated proximally relative to jaw members 210, 220 such that rollers 252, 254 are translated proximally along proximal support arms 214, 224, allowing jaw members 210, 220 to return to the spaced-apart position, as shown in FIG. 2A. Thus, end effector assembly 200 permits movement of jaw members 210, 220 between spaced-apart and approximated positions without the use of a pivot pin engaged therebetween.

Figure 3:
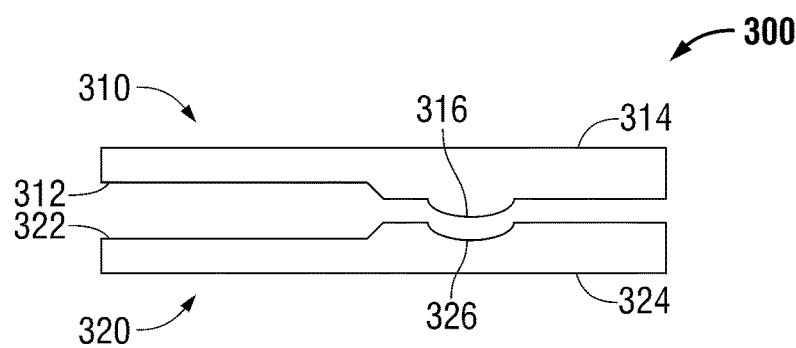
FIG. 3 is a side view of another end effector assembly configured for use with the forceps of FIG. 1.

Referring now to FIG. 3, another embodiment of an end effector assembly similar to end effector assembly 200 (FIGS. 2A-2B) is shown identified by reference numeral 300. End effector assembly 300 includes first and second jaw members 310, 320, each defining a respective electrically-conductive tissue sealing surface 312, 322 and including a respective proximal support arm 314, 324 extending proximally therefrom. Proximal support arm 314 of jaw member 310 includes a hemispherical protrusion 316 extending therefrom toward proximal support arm 324 of jaw member 320. Proximal support arm 324 includes a hemispherical recess 326 defined therein and configured to receive protrusion 316 of jaw member 310 therein such that jaw members 310 may pivot relative to jaw member 320 between a space-apart position and an approximated position. In particular, the engagement between the hemispherical-shaped protrusion 316 and recess 336 permits pivoting of jaw member 310 relative to jaw member 320. Thus, due to the structural configuration of jaw member 310, 320, jaw members 310, 320 are pivotable relative to one another without requiring a pivot pin-aperture engagement therebetween.

With continued reference to FIG. 3, in conjunction with FIG. 2B, similar to end effector assembly 200, proximal support arms 314, 324 of effector assembly 300 are configured for positioning within inner tube 250. Inner tube 250, as described above, is translatable relative to end effector assembly 300 and includes opposed rollers 252, 254. As can be appreciated, distal translation of inner tube 250 relative to end effector assembly 300, e.g., distally beyond protrusion and recess 316, 326, respectively, effects pivoting of hemispherical protrusion 316 within hemispherical recess 326 such that jaw member 310 is moved toward an approximated position relative to jaw member 310. On the other hand, as inner tube 250 is translated proximally beyond protrusion and recess 316, 326, respectively, jaw member 310 is pivoted relative to jaw members 320 back to the spaced-apart position. Further, jaw members 310, 320 of effector assembly 300 may be replaceable similarly as described above with respect to end effector assembly 200. The use of end effector assembly 300 is similar to that of end effector assembly 200, described above.

Figure 4A:
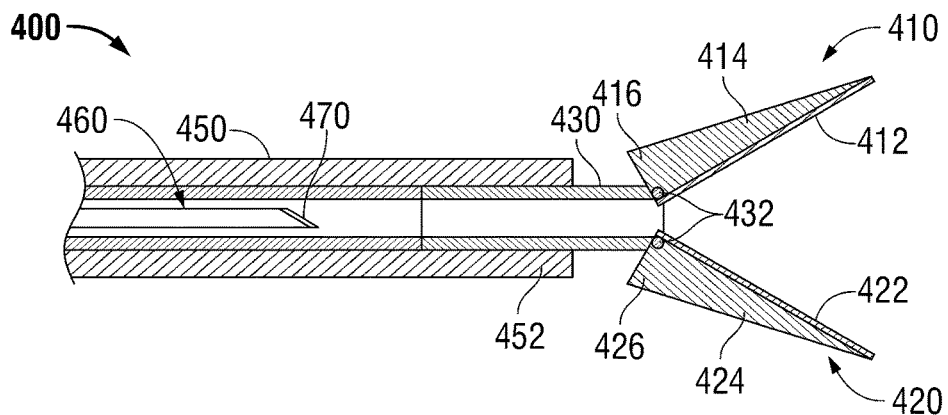
FIG. 4A is a longitudinal, cross-sectional view of still another end effector assembly provided in accordance with the present disclosure wherein jaw members of the end effector assembly are disposed in a spaced-apart position.
Figure 4B:
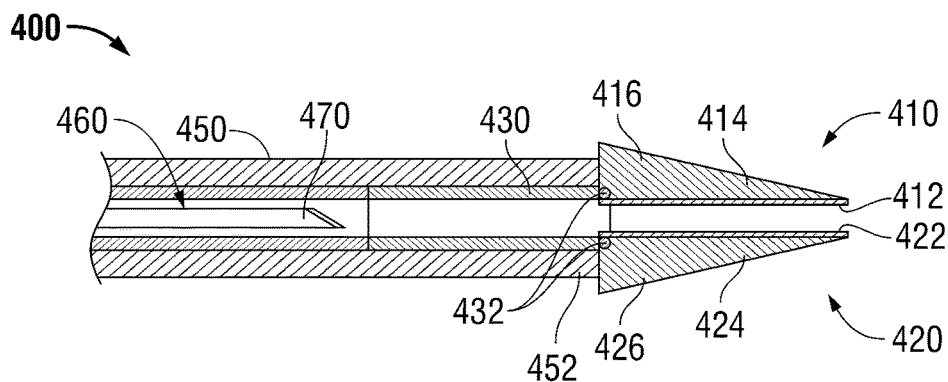
FIG. 4B is a longitudinal, cross-sectional view of the end effector assembly of FIG. 4A wherein the jaw members are disposed in an approximated position.
Figure 4C:
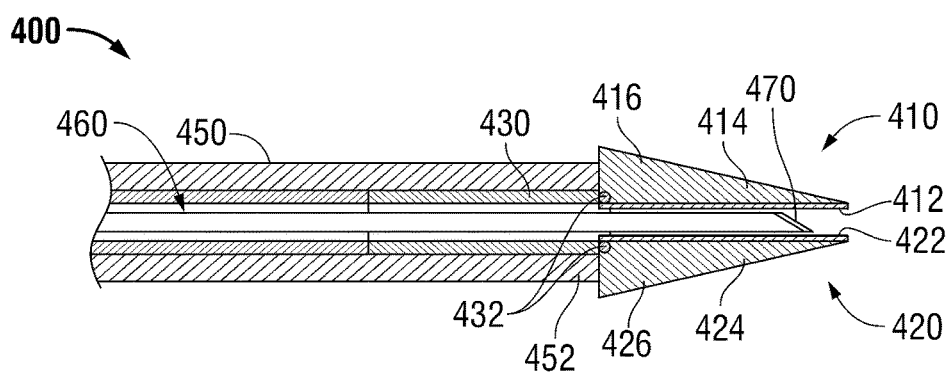
FIG. 4C is a longitudinal, cross-sectional view of the end effector assembly of FIG. 4A wherein a knife blade has been advanced between the approximated jaw members.

Turning now to FIGS. 4A-4C, another embodiment of an end effector assembly provided in accordance with the present disclosure is shown generally identified by reference numeral 400. End effector assembly 400 includes first and second jaw members 410, 420, respectively. Each jaw member 410, 420 includes an opposed electrically-conductive tissue sealing plate 412, 422 disposed thereon and an outer insulative jaw housing 414, 424, respectively. Each jaw member 410, 420 is pivotably, hingeably, or otherwise flexibly coupled, e.g., via a living hinge 432, to rod 430 at proximal ends 416, 426, respectively, thereof. Hinges 432 are positioned towards the inner, opposed surfaces of jaw members 410, 420 such that jaw housings 414, 424 extend outwardly from hinges 432 beyond rod 430. Jaw members 410, 420 are movable relative to one another between a spaced-apart position and an approximated position for grasping tissue therebetween. Further, as shown in FIG. 4A, jaw members 410, 420 may be biased toward the spaced-apart position.

With continued reference to FIGS. 4A-4C, end effector assembly 400 further includes a movable tube 450, similar to inner tube 250 (see FIG. 2B) that is longitudinally translatable relative to rod 430 and jaw members 410, 420. Movable tube 450 is configured for positioning within shaft 12 (FIG. 1) and is disposed about rod 430. Jaw housings 414, 424 of jaw members 410, 420, respectively, however, extend beyond movable tube 450, i.e., movable tube 450 is not positionable about jaws 410, 420, respectively. Movable tube 450 is longitudinally translatable, e.g., via depression of movable handle 40 (FIG. 1), between a retracted position (see FIG. 4A) and an extended position (see FIGS. 4B-4C) for moving jaw members 410, 420 between the spaced-apart and approximated positions. More specifically, upon distal translation of movable tube 450, distal end 452 of movable tube 450 eventually contacts proximal ends 416, 426 of jaw housings 414, 424 of jaw members 410, 420, respectively. Upon further distal translation of movable tube 450, movable tube 450 urges proximal ends 416, 426 of jaw members 410, 420, respectively, distally such that jaw members 410, 420 are pivoted about hinges 432, thereby moving jaw members 410, 420 from the spaced-apart position to the approximated position, as shown in FIG. 4B, to grasp tissue therebetween. Similarly as described above, with tissue grasped between jaw members 410, 420, energy may be supplied to one or both of sealing plates 412, 422 of jaw members 410, 420, respectively, to effect a tissue seal.

When it is desired to move jaw members 410, 420 back to the spaced-apart position, movable tube 450 is translated proximally, e.g., by releasing movable handle 40 (FIG. 1). Once movable tube 450 has been translated sufficiently in the proximal direction, jaw housings 414, 424 are no longer urged proximally to pivot jaw members 410, 420 about hinges 432 to the approximated position and, thus, jaw members 410, 420 are permitted to return under bias back to the spaced-apart position.

End effector assembly 400 may further include a knife assembly 460 disposed within shaft 12 (FIG. 1) that is translatable relative to rod 430 and jaw members 410, 420 between a retracted position, wherein knife blade 470 of knife assembly 460 is positioned proximally of jaw members 410, 420 (FIG. 4B), e.g., within rod 430, and an extended position, wherein knife blade 470 is advanced between jaw members 410, 420 to cut tissue grasped therebetween (FIG. 4C). Knife blade 470 may be selectively actuated by activation of trigger 72 of trigger assembly 70 (see FIG. 1).

Figure 5:
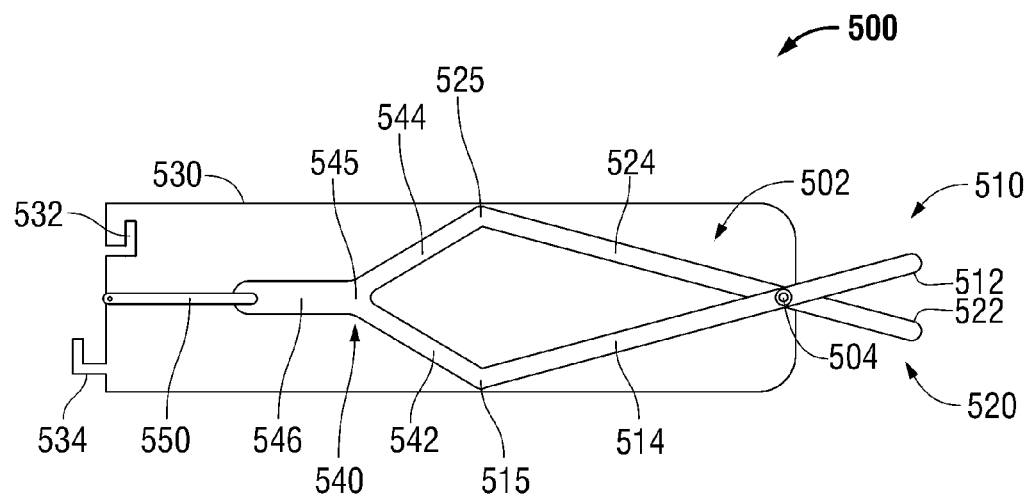
FIG. 5 is a longitudinal, cross-sectional view of another end effector assembly configured for use with the forceps of FIG. 1.

Turning now to FIG. 5, another embodiment of an end effector assembly, end effector assembly 500, configured for use with forceps 10 (FIG. 1) (or any other suitable surgical instrument) is shown. End effector assembly 500 includes an outer tube 530 that is configured to releasably engage distal end 14 (FIG. 1) of shaft 12 (FIG. 1), e.g., via the engagement of twist-locking components 532, 534 of outer tube 530 with complementary lock components (not explicitly shown) disposed at distal end 14 (FIG. 1) of shaft 12 (FIG. 1).

A jaw assembly 502 is disposed within outer tube 530 and includes a pair of jaw members 510, 520 extending distally from outer tube 530. Jaw members 510, 520 are pivotably coupled to one another about a pivot pin 504 that is fixed relative to outer tube 530. Jaw members 510, 520 are pivotable about pivot pin 504 and relative to each other between a spaced-apart position and an approximated position for grasping tissue therebetween. Each jaw member 510, 520 includes an electrically-conductive tissue sealing surface 512, 522, respectively, defined on an opposed surface thereof. Jaw members 510, 520 each further include a proximal shaft 514, 524 extending proximally beyond pivot pin 504. Proximal shafts 514, 524, in turn, are engaged to first and second prongs 542, 544, respectively, of Y-link 540 at the proximal ends thereof via living hinges 515, 525 (although other suitable linkages are also contemplated). First and second prongs 542, 544 of Y-link 540 are coupled to one another via living hinge 545. Third prong 546 of Y-link 540 extends proximally from living hinge 545 and is coupled to drive rod connector 550 at the proximal end thereof. Drive rod connector 550 is configured to releasably engage the drive assembly (not explicitly shown) of forceps 10 (FIG. 1) during coupling of outer tube 530 to distal end 14 (FIG. 1) of shaft 12 (FIG. 1) such that depression of movable handle 40 (FIG. 1) translates drive rod connector 550 proximally.

With jaw members 510, 520 coupled to one another about fixed pivot pin 504, as can be appreciated, translation of drive rod connector 550, e.g., upon depression of movable handle 40 (FIG. 1), effects movement of prongs 542, 544, 546 of Y-link 540 relative to one another. More specifically, proximal translation of drive rod connector 550 pulls third prong 546 proximally such that first and second prongs 542, 544 are pivoted about living hinge 545 toward one another. The pivoting of first and second prongs 542, 544 towards one another urges living hinges 515, 525 toward one another such that proximal shafts 514, 524 are moved toward one another. The approximation of proximal shafts 514, 524, in turn, pivots jaw members 510, 520 about pivot pin 504 toward the approximated position to grasp tissue therebetween. Energy may thereafter be supplied to tissue grasped between jaw members 510, 520 to effect a tissue seal.

In order to return jaw members 510, 520 to the spaced-apart position, drive rod connector 550 is urged distally, e.g., by releasing, or returning movable handle 40 (FIG. 1), such that first and second prongs 542, 544, respectively, are urged apart from one another. As first and second prongs 542, 544, respectively, are urged apart from one another, jaw members 510, 520 are likewise urged apart from one another back toward the spaced-apart position. Jaw members 510, 520 may be biased toward the spaced-apart position due to the bias of Y-link 540. Further, as shown in FIG. 5, the spacing between jaw members 510, 520 in the spaced-apart position may be defined by the internal dimensions of outer tube 530. In other words, the internal dimensions of outer tube 530 may be inhibit separation of first and second prongs 542, 544 of Y-link 540 beyond a specific range, thus inhibiting further spacing of jaw members 510, 520.

As can be appreciated, end effector assembly 500 is advantageous in that, since living hinges are used, jaw assembly 502, including jaw members 510, 520, proximal shafts 514, 524, and Y-link 540, may be formed as a single component having a plurality of living hinges. Such a configuration reduces the overall component count of end effector assembly 500 and facilitates cleaning and sterilization of end effector assembly 500. Further, end effector assembly 500 may be replaced with a new end effector assembly 500 by de-coupling drive bar connector 500 and outer tube 530 from the drive assembly (not explicitly shown) and shaft 12 (FIG. 1), respectively, and engaging a new end effector assembly 500 thereon, thus obviating the need for substantial assembly of various different components.

Figure 6:
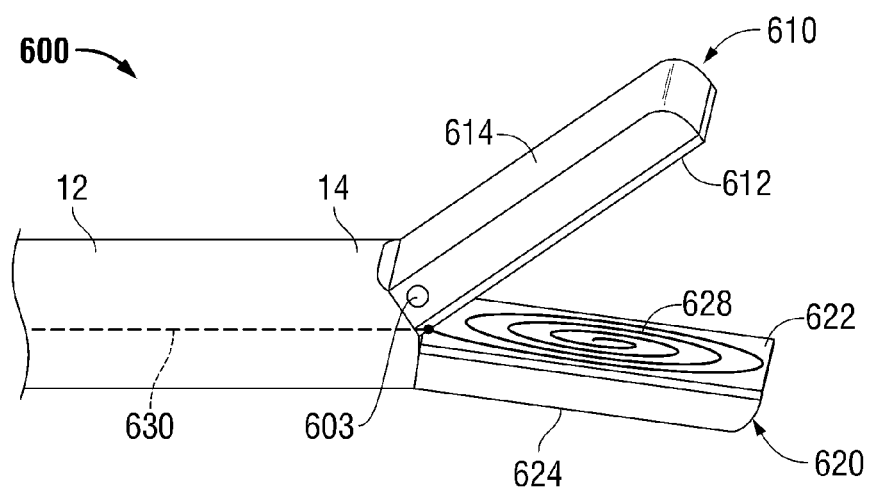
FIG. 6 is a side, perspective view of still another end effector assembly configured for use with the forceps of FIG. 1.

Referring now to FIG. 6, still yet another embodiment of an end effector assembly configured for use with forceps 10 (FIG. 1) is shown generally identified by reference numeral 600. End effector assembly 600 is disposed at distal end 14 of shaft 14 and includes first and second jaw members 610, 620 pivotably coupled to one another via pivot 603 and movable relative to one another between a spaced-apart position and an approximated position for grasping tissue therebetween. Each jaw member 610, 620 includes an insulative outer jaw housing 614, 624, e.g., a ceramic outer housing, and an opposed electrically-conductive tissue sealing plate 612, 622, respectively. One (or both) of the jaw members 610, 620, e.g., jaw member 620, may further include an inductive coil 628 disposed within jaw housing 624 adjacent sealing plate 622. Inductive coil 628 is coupled to a source of energy, e.g., via a wire 630 extending from jaw member 620 through shaft 12 and ultimately coupling to the source of energy (not explicitly shown). In use, when inductive coil 628 is supplied with energy, inductive coil 628 energizes tissue sealing plate 622. Tissue sealing plate 622, in turn, conducts energy through tissue grasped between sealing plates 612, 622 of jaw members 610, 620, respectively, to treat, e.g., seal, tissue grasped therebetween.

Figure 7:
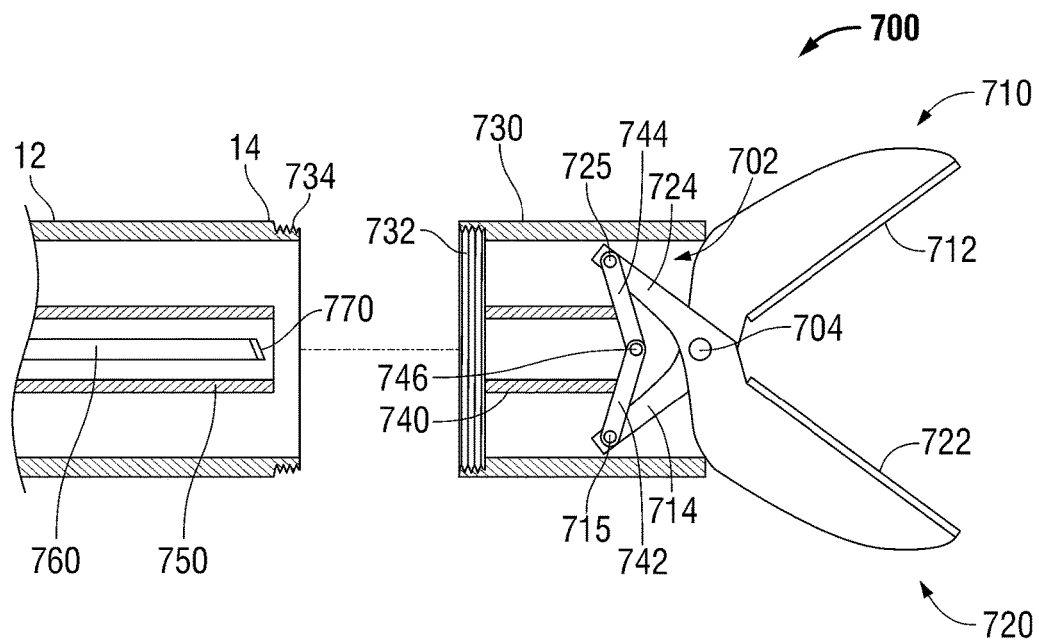
FIG. 7 is a longitudinal, cross-sectional view of yet another end effector assembly configured for use with the forceps of FIG. 1.

With reference now to FIG. 7, another embodiment of an end effector assembly provided in accordance with the present disclosure is shown generally identified by reference numeral 700. End effector assembly 700 is releasably couplable to distal end 14 of shaft 12, as will be described in detail below, to permit replacement of end effector assembly 700 after each use or to facilitate cleaning and sterilization of end effector assembly 700 for reuse.

End effector assembly 700 includes a jaw assembly 702 disposed within an outer tube 730. Outer tube 730 is configured to releasably engage distal end 14 of shaft 12, e.g., via threaded, bayonet, or other suitbale coupling of components 732, 734 to one another. Jaw assembly 702 includes first and second jaw members 710, 720 extending distally from outer tube 730. Jaw members 710, 720 each include a proximal arm 714, 724, respectively, that is disposed within outer tube 730, and a respective electrically conductive tissue sealing plate 712, 722 disposed on an opposed surface thereof. Tissue sealing plate 712 and/or tissue sealing plate 722 are adapted to connect to a source of energy for treating, e.g., sealing, tissue grasped therebetween. Jaw members 710, 720 are pivotably coupled about a fixed pivot pin 704 engaged within outer tube 730. Jaw members 710, 720 are movable about pin pivot 704 relative to one another between a spaced-apart position and an approximated position for grasping tissue therebetween.

With continued reference to FIG. 7, outer tube 730 includes a drive bar connector 740 disposed therein and coupled to jaw members 710, 720. Drive bar connector 740 is pivotably coupled to proximal arm 714 of jaw member 710 via first linkage 742 and to proximal arm 724 of jaw member 720 via second linkage 744. Further, first and second linkages 742, 744, respectively, are coupled to drive bar connector 740 about pivot pin 746 and are coupled to proximal arms 714, 724, respectively, via pivots 715, 725, respectively. Pivot pin 746 is fixedly engaged to drive bar connector 740 at the distal end thereof. As a result of this configuration, longitudinal translation of translation of drive bar connector 740 urges linkages 742, 744 to pivot about pivot pin 746 between a more transversely-aligned position, and a more longitudinally-parallel position. As linkages 742, 744 are moved between these positions, proximal arms 714, 724 of jaw members 710, 720 are moved relative to one another such that jaw members 710, 270 are pivoted about pivot pin 704 between the spaced-apart position and the approximated position.

In use, end effector assembly 700 is first engaged to distal end 14 of shaft 12. At the same time, or thereafter, drive bar connector 740 is coupled to drive bar 750 of forceps 10 via any suitable mechanism, e.g., friction fitting, threaded coupling, snap-fitting, etc. Drive bar 750, in turn, is coupled to the drive assembly (not explicitly shown) of forceps 10 (FIG. 1), as mentioned above. Accordingly, with drive bar connector 740 coupled to drive bar 750, drive bar 750 may be translated through shaft 12, e.g., via depression of movable handle 40 (FIG. 1), to effect similar translation of drive bar connector 740, thereby moving jaw members 710, 720 between the spaced-apart position and the approximated position for grasping tissue therebetween. Drive bar 750 and drive bar connector 740 may further cooperate to permit reciprocation of knife blade 770 of knife assembly 760 therethrough, e.g., upon activation of trigger actuator 72 (FIG. 1) of trigger assembly 70 (FIG. 1), to cut tissue grasped between jaw members 710, 720.

Figure 8:
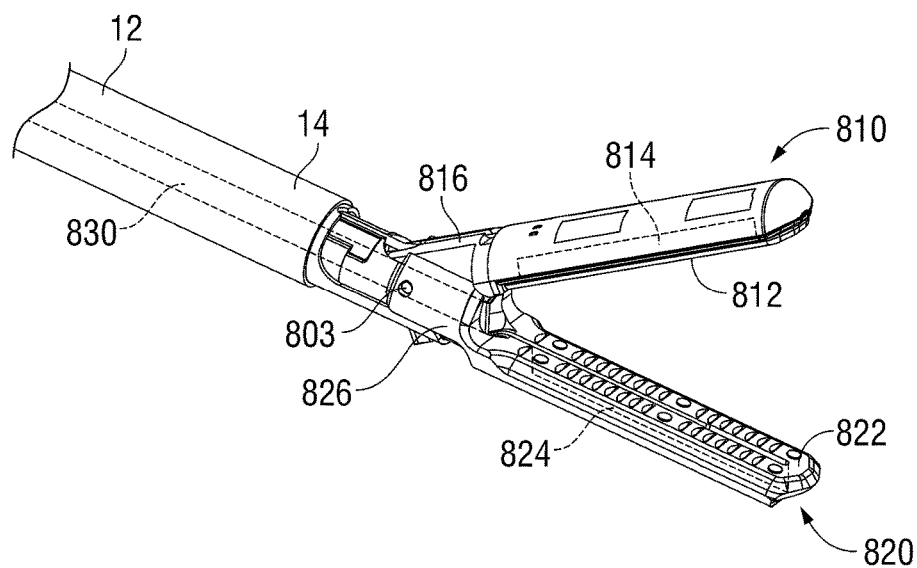
FIG. 8 is a longitudinal, cross-sectional view of another end effector assembly configured for use with the forceps of FIG. 1.

Turning now to FIG. 8, another embodiment of an end effector assembly configured for use with forceps 10 (FIG. 1) is shown generally identified by reference numeral 800. End effector assembly 800 is disposed at distal end 14 of shaft 12 and includes opposing jaw members 810 and 820, each of which includes an electrically conductive tissue sealing plate 812, 822, respectively, disposed thereon. Jaw members 810, 820 are movable about pivot 803 between a spaced-apart position and an approximated position for grasping tissue therebetween. Tissue sealing plates 812, 822 are adapted to conduct energy through tissue grasped therebetween to effect a tissue seal. Jaw members 810, 280 may each further include a longitudinal channel 814, 824 defined through tissue sealing plates 812, 822, respectively, thereof. Channels 814, 824 may define mirrored, reflective, or otherwise configured inner surfaces, the importance of which will be described in greater detail below.

Continuing with reference to FIG. 8, a light tube 830 extends through shaft 12 to proximal ends 816, 826 of jaw members 810, 820, respectively. Light tube 830 is configured to transmit light energy from a light source (not explicitly shown), e.g., a generator, between jaw members 810, 820, respectively, e.g., into channels 814, 824 of jaw members 810, 820, respectively, to cut tissue grasped therebetween. Mirrored, reflective, or otherwise configured inner surfaces of channels 814, 824 may facilitate the application of light energy to tissue disposed between jaw members 810, 820, thus facilitating the division of tissue grasped therebetween. In some embodiments, light energy may also be used to effect a tissue seal.

Figure 9:
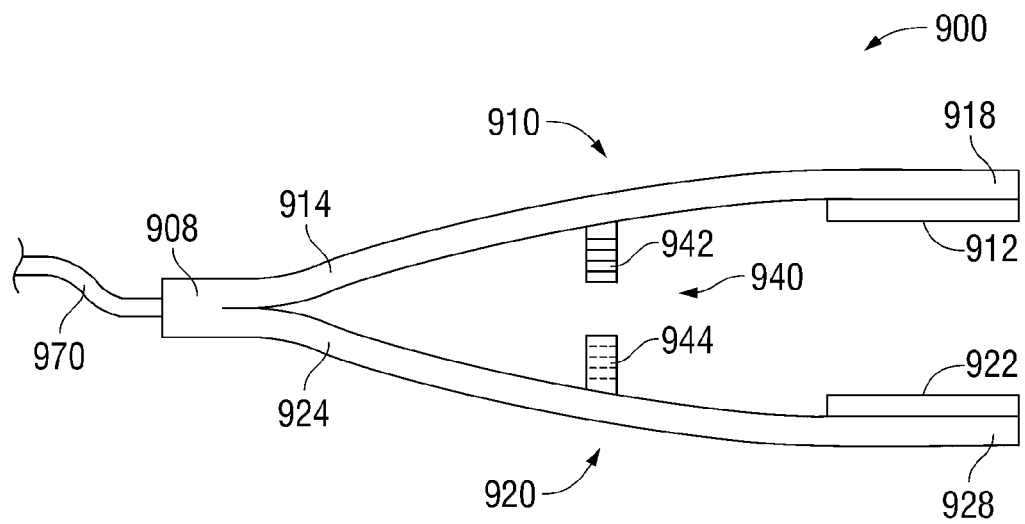
FIG. 9 is a side view of another forceps provided in accordance with the present disclosure.

Turning now to FIG. 9, another embodiment of a forceps provided in accordance with the present disclosure is shown generally identified by reference numeral 900. Forceps 900 includes first and second arms 910, 920, respectively. Arms 910, 920 are coupled at the proximal ends 914, 924, respectively, thereof, e.g., via adhesion, welding, latching, or any other suitable mechanism, or may be formed together at proximal ends 914, 924, respectively, thereof as a single component including a living hinge 908 interconnecting arms 910, 920.

Arms 910, 920 each further include an electrically-conductive tissue sealing plate 912, 922, respectively, disposed towards the distal ends 918, 928, respectively, thereof. Sealing plates 912, 922 may be electrically coupled to a source of energy, e.g., via a wire or wires 970 extending through arms 910, 920 that ultimately couple to the source of energy (not shown), for conducting energy through tissue grasped therebetween to treat, e.g., seal, tissue. Arms 910, 920 are formed at least partially from a flexible material and are biased towards a spaced-apart position, as shown in FIG. 9. In order to move arms 910, 920 into approximation with one another to grasp tissue between sealing plates 912, 922, arms 910, 920 may be squeezed toward one another at an intermediate position between proximal and distal ends 914, 924 and 918, 928, respectively, thereof. Thereafter, energy may be supplied to sealing plates 912, 922 to treat, as mentioned above.

Forceps 900 may further include a ratchet assembly 940 disposed distally of living hinge 908 that includes first and second ratchet components 942, 944 that are incrementally engagable with one another to achieve a consistent and accurate closure pressure between sealing plates 912, 922 of arms 910, 920, respectively, during tissue sealing. Ratchet assembly 940 may also define a pre-determined limit position, inhibiting further engagement of ratchet components 942, 944 to one another beyond the pre-determined limit position, to thereby define a minimum gap distance between jaw members 910, 920.

As can be appreciated, the simplified construction and reduced number of components of forceps 900 reduces the costs associated with manufacturing forceps 900 and also facilitates the cleaning and sterilization of forceps 900 for reuse. Alternatively, given the relatively low manufacturing costs of forceps 900, forceps 900 may be used as a disposable instrument.

Figure 10:
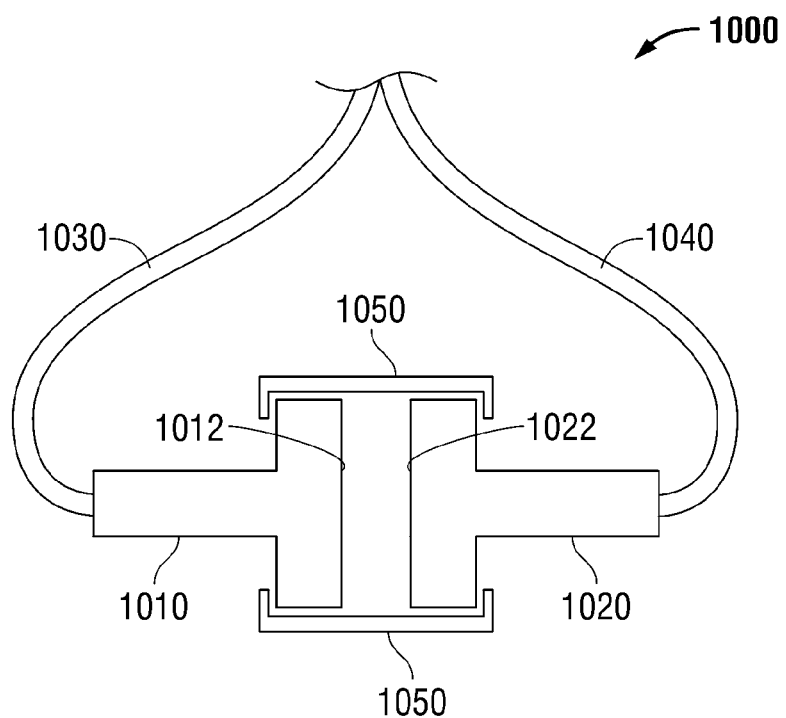
FIG. 10 is a side view of still another forceps provided in accordance with the present disclosure.

FIG. 10 shows another embodiment of a forceps-like device 1000 that includes first and second paddles 1010, 1020, respectively. Each paddle 1010, 1020 includes an opposed electrically-conductive tissue sealing surface 1012, 1022 and a cable 1030, 1040 coupled thereto that is adapted to couple the tissue sealing surfaces 1012, 1022, respectively, to a source of energy for treating, e.g., sealing, tissue disposed between paddles 1010, 1020. Alternatively, paddles 1010, 1020 may be formed from a conductive material and may be coated, except for tissue sealing surfaces 1012, 1022, with an insulative material. Cables 1030, 1040 may ultimately be mechanically connected to one another to maintain the components of forceps-like device 1000 together. In other words, cables 1030, 1040 may be joined to one another, as shown in FIG. 10, to help prevent misplacement or separation of first and second paddles 1010, 1020, respectively, from one another. Further, one or more clamp members 1050 may be provided for clamping paddles 1010, 1020 to one another with tissue grasped therebetween to achieve a consistent and accurate closure pressure between sealing surfaces 1012, 1022. As such, multiple different clamp members 1050 of various sizes may be provided for achieving a desired closure pressure between paddles 1010, 1020 about tissues of different sizes. Further, tissue sealing surfaces 1012, 1022 may include stop features (not explicitly shown), e.g., ceramic stop members, disposed thereon for maintaining a minimum gap distance between sealing surfaces 1012, 1022. Alternatively, or additionally, clamp members 1050 may include stop features (not explicitly shown) configured to define a minimum gap distance between sealing surfaces 1012, 1022.

In use, paddles 1010, 1020 are positioned on either side of tissue to be treated and are approximated relative to one another. One or more clamp members 1050 are then clamped about paddles 1010, 1020 to retain paddles 1010, 1020 in position relative to one another grasping tissue therebetween. Such a configuration helps maintain a pre-determined gap distance and/or closure pressure between sealing surfaces 1012, 1022 of paddles 1010, 1020, respectively. The minimum gap distance between sealing surfaces 1012, 1022 during tissue sealing may be between about 0.001 inches and about 0.006 inches, while the closure pressure during tissue sealing may be in the range of about 3 $kg/cm^2$ to about 16 $kg/cm^2$. With tissue grasped between paddles 1010, 1020 and with clamp members 1050 retaining paddles 1010, 1020 in position, energy may be supplied from cables 1030, 1040 and conducted through tissue to effect a tissue seal.

Figure 11:
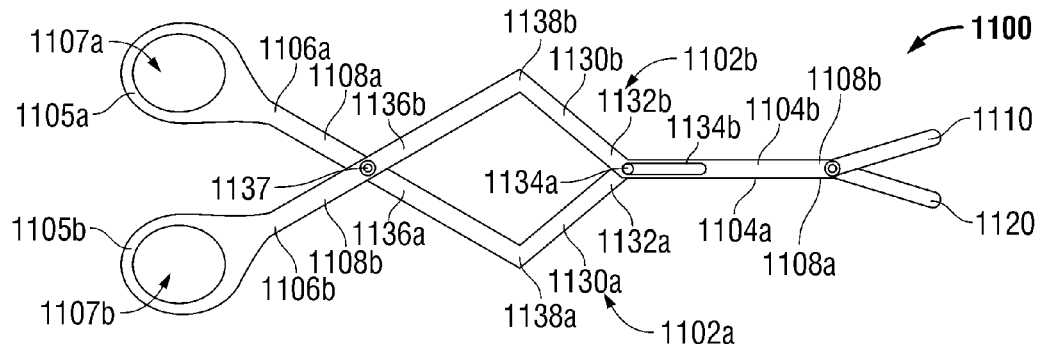
FIG. 11 is a side view of yet another forceps provided in accordance with the present disclosure.

Still yet another embodiment of a forceps provided in accordance with the present disclosure is shown in FIG. 11 generally identified by reference numeral 1100. Forceps 1100 includes first and second shafts 1102a, 1102b, each including a jaw member 1110, 1120 disposed at the distal end thereof. Shafts 1102a, 1102b each further include a handle 1105a, 1105b disposed at a proximal end 1106a, 1106b, respectively, thereof, that each define a respective finger hole 1107a, 1107b therethrough to facilitate grasping of forceps 1100.

More specifically, shafts 1102a, 1102b of forceps 1100 each include a substantially straight distal segment 1104a, 1104b, a proximal segment 1108a, 1108b, and an elbow segment 1130a, 1130b interconnecting proximal and distal segments 1108a, 1108b and 1104a, 1104b, respectively, of shafts 1102a, 1102b. Distal segments 1104a, 1104b are configured for insertion through an opening in tissue and into an internal surgical site for use in endoscopic surgical procedures, although forceps 1100 may also be configured for use in open surgical procedures. Distal segments 1104a, 1104b includes jaw members 1110, 1120, respectively, that are pivotably coupled to one another towards the distal ends thereof. Proximal segments 1108a, 1108b extend proximally from elbow segments 1130a, 1130b, respectively, and include handles 1105a, 1105b disposed thereon.

Elbow segments 1130a, 1130b are slidably coupled to one another at first ends 1132a, 1132b, respectively thereof via a pin-slot engagement, e.g., elbow segment 1130a includes a pin 1134a disposed within and translatable along slot 1134b defined within elbow segment 1130b, although this configuration may be reversed, and are pivotably coupled to one another at second ends 1136a, 1136b, respectively, thereof via pivot 1137. Elbow segments 1130a, 1130b each further include a hinge 1138a, 1138b, e.g., a living hinge or pivot, disposed between first and second ends 1132a, 1132b and 1136a, 1136b, respectively thereof.

Due to the above described configuration, the surgeon may pivot jaw members 1110, 1120 between a spaced-apart position and an approximated position by manipulating handles 1105a, 1105b relative to one another. More specifically, moving handles 1105a, 1105b towards one another pivots elbow segments 1130a, 1130b about pivot 1137 such that hinges 1138a, 1138b are moved toward one another. The pivoting of hinges 1138a, 1138b, in turn, urges elbow segments 1130a, 1130b distally such that pin 1134a is translated along slot 1134b. As pin 1134 is translated distally, distal segment 1104a is likewise translated distally such that jaw members 1110, 1120 are urged to pivot relative to each other from the spaced-apart position to the approximated position to grasp tissue therebetween.

In order to return jaw members 1110, 1120 to the spaced-apart position, handles 1105a, 1105b are moved apart from one another such that hinges 1138a, 1138b are likewise moved apart from one another, thereby pulling distal segment 1104a proximally and returning jaw members 1110, 1120 back to the spaced-apart position. As can be appreciated, forceps 1100 provides a simplified endoscopic forceps that includes minimal components, which reduces the overall manufacturing cost and also facilitates sterilization of the instrument for reuse.

Figure 12:
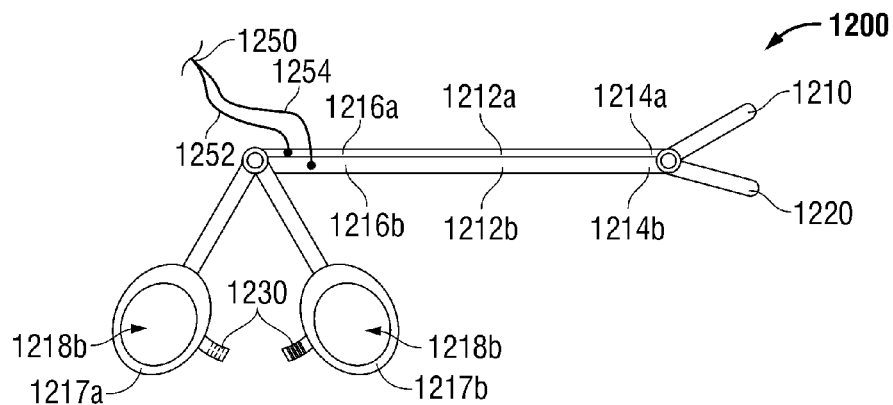
FIG. 12 is a side view of still yet another forceps provided in accordance with the present disclosure.

Referring now to FIG. 12, another embodiment of a forceps 1200 is shown including two elongated shafts 1212a, 1212b, each having a proximal end 1216a, 1216b, and a distal end 1214a, 1214b, respectively. Shafts 1212a, 1212b may be concentric with one another, i.e., one shaft may be disposed within or about the other, or may be positioned side-by-side. Each shaft 1212a, 1212b includes a handle 1217a, 1217b disposed at the proximal end 1216a, 1216b thereof. Each handle 1217a, 1217b defines a finger hole 1218a, 1218b therethrough for receiving a finger of the user. Shafts 1212a, 1212b each further include a jaw member 1210, 1220, respectively, disposed at respective distal ends 1214a, 1214b thereof. Jaw members 1210, 1220 are pivotable relative to one another about a pivot between a spaced-apart position and an approximated position for grasping tissue therebetween. A ratchet 1230 may also be included for selectively locking jaw members 1210 and 1220 relative to one another at various positions during pivoting. Ratchet 1230 may include graduations or other visual markings that enable the user to easily and quickly ascertain and control the amount of closure force desired between jaw members 1210, 1220.

With continued reference to FIG. 12, shafts 1212a, 1212b and jaw members 1210, 1220 are formed at least partially from an electrically conductive material, e.g., stainless steel. Accordingly, a cable 1250 includes first and second wires 1252, 1254 may be coupled directly to one or both of shafts 1212a, 1212b, e.g., via clamping, such that energy may be conducted between jaw members 1210, 1220 and through tissue grasped therebetween to treat tissue, e.g., to effect a tissue seal. Such a configuration permits simplified coupling of cable 1250 to forceps 1200 and eliminates the need for complex electrical connections for supplying energy to jaw members 1210, 1220. This configuration also allows for a reduced and simplified component count, obviates the need to disassemble forceps 1200 for sterilization, and reduces the manufacturing costs associated with manufacturing forceps 1200.

Figure 13:
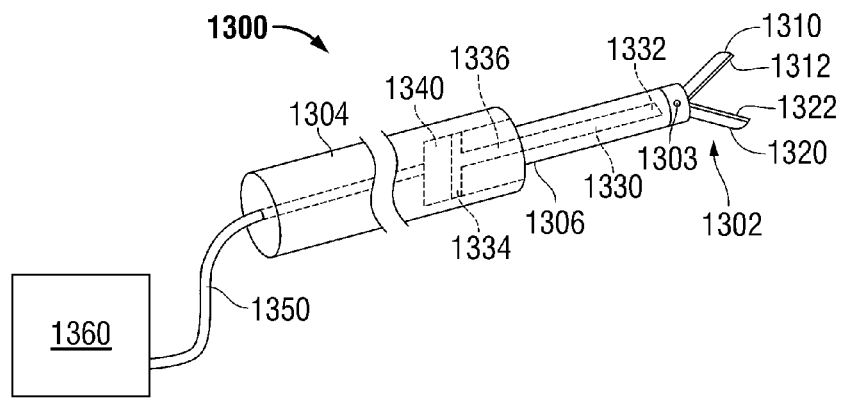
FIG. 13 is a side, perspective view of another forceps provided in accordance with the present disclosure.

With reference now to FIG. 13, yet another embodiment of a forceps provided in accordance with the present disclosure is shown generally identified by reference numeral 1300. Forceps 1300 includes an end effector assembly 1302 a housing 1304 and a shaft 1306 interconnecting housing 1304 and end effector assembly 1306. End effector assembly 1302, similar to end effector assembly 100 (FIG. 1), includes opposing jaw members 1310 and 1320, each of which includes an electrically conductive tissue sealing plate 1312, 1322, respectively, disposed thereon. Jaw members 1310, 1320 are movable about pivot 1303 between a spaced-apart position and an approximated position for grasping tissue therebetween. Tissue sealing plates 1312, 1322 are adapted to conduct energy through tissue grasped therebetween to treat tissue, e.g., to effect a tissue seal.

A drive bar 1330 extending through shaft 1306 is coupled to one or both of jaw members 1310, 1320 at distal end 1332 thereof and is selectively translatable relative to end effector assembly 1302 to pivot jaw members 1310, 1320 between the spaced-apart and approximated positions. Drive bar 1330 further includes a piston stop 1334 disposed at proximal end 1336 thereof. Piston stop 1334 is disposed within pneumatic, or piston cylinder 1340 in sealing relation therewith which, in turn, is disposed within housing 1304. Piston stop 1334 is selectively translatable within piston cylinder 1340 between a proximal position and a distal position to translate drive bar 1330, thereby moving jaw members 1310, 1320 between the spaced-apart and approximated positions. Piston cylinder 1340 is coupled, via cable 1350, to pneumatic energy source, or generator 1360. As can be appreciated, generator 1360 selectively pneumatically pressurizes, or depressurizes piston cylinder 1340 to selectively translate piston stop 1334 which, in turn, moves jaw members 1310, 1320 between the spaced-apart and approximated positions. Thus, manual actuation of jaw members 1310, 1320 is obviated in favor of a pneumatically-powered drive mechanism. Generator 1360 may also be configured to supply energy to tissue sealing plates 1312, 1322 of jaw members 1310, 1320, respectively, to treat, e.g., seal, tissue grasped therebetween. Further, as an alternative to piston stop 1334 and piston cylinder 1340, generator 1360 may be coupled to a bellows (not shown) for selectively translating drive bar 1330. The above-described configuration may similarly be used to selectively translate a knife blade between a retracted position and an extended position to cut tissue grasped between jaw members 1310, 1320.

Figure 14A:
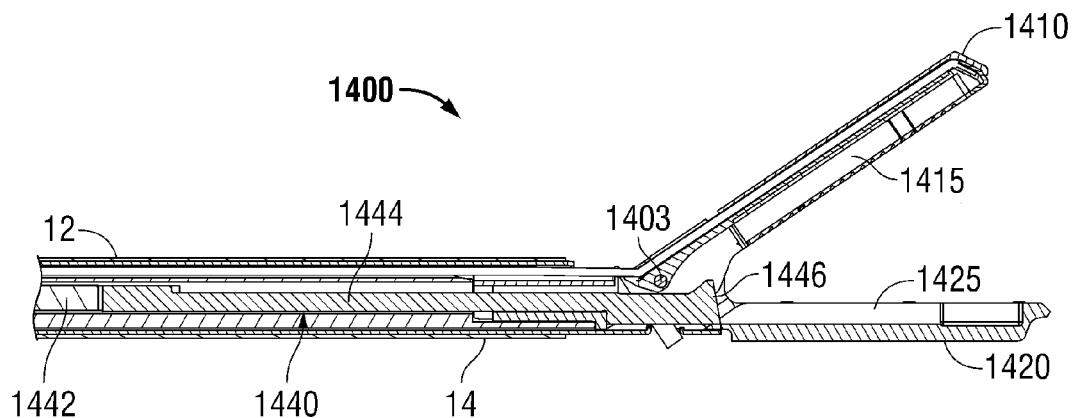
FIG. 14A is a longitudinal, cross-sectional view of still another end effector assembly provided in accordance with the present disclosure wherein jaw members of the end effector assembly are disposed in a spaced-apart position and a knife blade is in a retracted position.
Figure 14B:
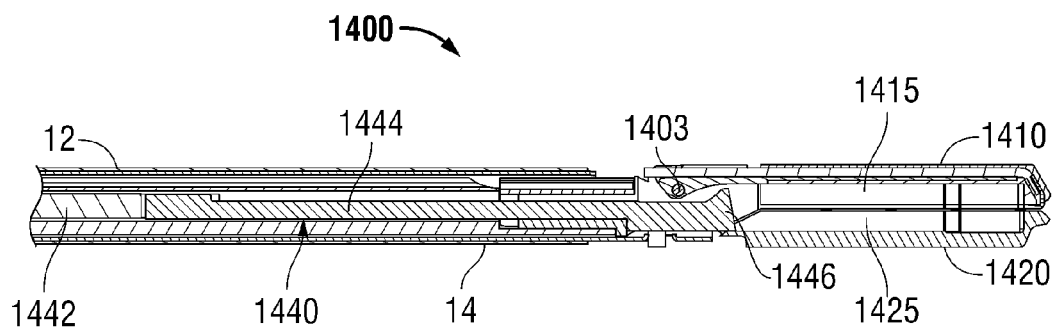
FIG. 14B is a longitudinal, cross-sectional view of the end effector assembly of FIG. 14A wherein the jaw members are disposed in an approximated position and the knife blade is in the retracted position.
Figure 14C:
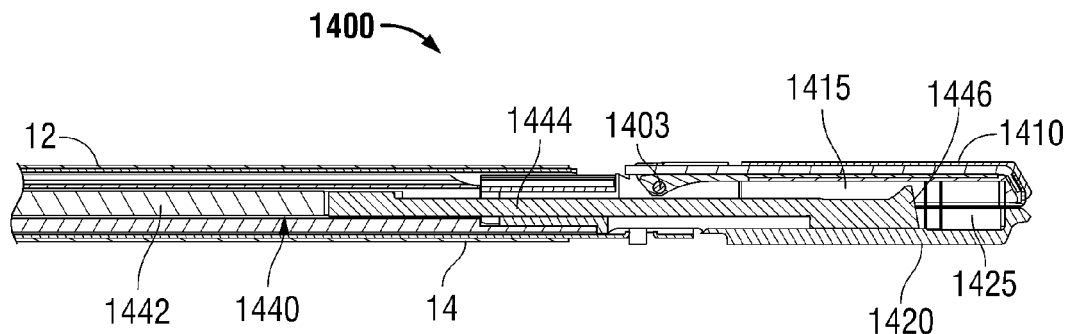
FIG. 14C is a longitudinal, cross-sectional view of the end effector assembly of FIG. 14A wherein the jaw members are disposed in the approximated position and the knife blade is in an extended position.

Turning now to FIGS. 14A-14C, an end effector assembly 1400 similar to end effector assembly 100 (FIG. 1) and configured for use with forceps 10 (FIG. 1) is shown including a knife assembly 1440 for cutting tissue disposed between jaw members 1410, 1420, respectively. Knife assembly 1440 includes a knife bar 1442 that is selectively translatable through shaft 12, e.g., upon activation of actuation trigger 72 (FIG. 1) of trigger assembly 70 (FIG. 1). Knife bar 1442 includes a knife 1444 coupled thereto and extending distally therefrom. Knife 1444 defines a cutting blade 1446 at the distal end thereof. As will be described below, knife bar 1442 is translatable to translate cutting blade 1446 between a retracted position, wherein cutting blade 1446 is disposed within shaft 12, and an extended position, wherein cutting blade 1446 extends through blade channels 1415, 1425 of jaw members 1410, 1420, respectively, to cut tissue grasped therebetween.

Initially, with jaw members 1410, 1420 disposed in the spaced-apart position, as shown in FIG. 14A, cutting blade 1446 is disposed in the retracted position. However, once jaw members 1410, 1420 are moved to the approximated position to grasp tissue therebetween, as shown in FIGS. 14B-14C, cutting blade 1446 may be advanced from the retracted position (FIG. 14B) to the extended position (FIG. 14C) to cut tissue grasped between jaw members 1410, 1420.

Various configurations of knife assemblies and end effector assemblies similar to knife assembly 1440 and end effector assembly 1400 will be described in detail below with reference to FIGS. 15-22. In particular, the end effector and knife assemblies described below facilitate the engagement and disengagement of at least a portion of the knife assembly for cleaning and re-engaging the knife assembly, or for replacing the knife assembly (or components thereof) with a new knife assembly in preparation for re-use. Further, the end effector and knife assemblies described herein are configured to permit replacement, disengagement and re-engagement of the knife assemblies or components thereof while the end effector assembly remains in a substantially assembled condition, i.e., without requiring substantial disassembly of the end effector assembly.

Figure 15:
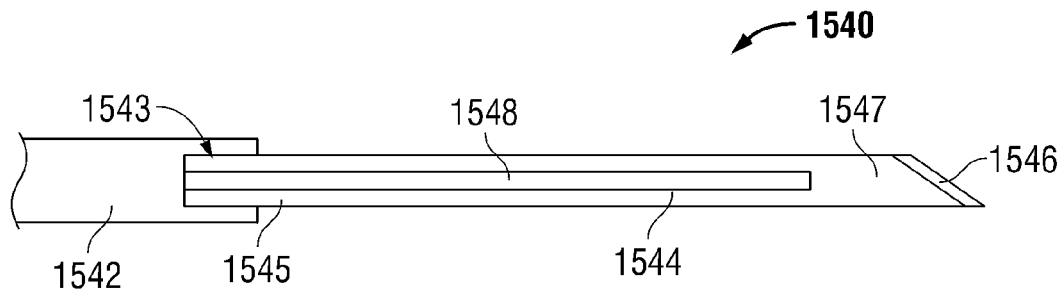
FIG. 15 is a side view of another knife assembly provided in accordance with the present disclosure.

As shown in FIG. 15, in conjunction with FIGS. 14A-14C, knife assembly 1540 includes a first, or proximal component 1542 and a second, or distal component 1544. More specifically, distal component 1544 of knife assembly 1540 is engaged to knife bar 1542 at proximal end 1545 thereof and includes a cutting blade 1546 defined at distal end 1547 thereof. Distal component, or knife 1544 is releasably engaged within recess 1543 of knife bar 1542, e.g., via friction fitting, or any of the configurations described below with respect to FIGS. 18-20. Further, knife 1544 includes a slot 1548 extending longitudinally therethrough from proximal end 1545 thereof. As such, knife 1544 defines an open proximal end 1545. Slot 1548 is configured to receive pivot pin 1403 of end effector assembly 1400 therethrough. In this configuration, knife 1544 need not pass around, e.g., above or below, pivot pin 1403, but may be disposed about pivot pin 1403 with pivot pin 1403 disposed within slot 1548, thus permitting knife 1544 to be translated between the retracted and extended positions for cutting tissue grasped between jaw members 1410, 1420.

Open proximal end 1545 of knife 1544 permits knife 1544 to be disengaged from proximal component, or knife bar 1542 and moved distally to remove knife 1544 from end effector assembly 1400. More specifically, as knife 1544 is moved distally, pivot pin 1403 is translated along slot 1548, ultimately exiting slot 1548 at open proximal end 1545 of knife 1544, thus disengaging knife 1544 from pivot pin 1403. Such a configuration facilitates the removal of knife 1544 from end effector assembly 1400 without requiring significant disassembly of end effector assembly 1400. Further, this configuration facilitates replacement of knife 1544 in that, in order to install a new knife 1544, knife 1544 is advanced proximally through end effector assembly 1400 such that pivot pin 1403 is disposed within slot 1548. Knife 1544 is then advanced further proximally into engagement with knife bar 1542, e.g., frictional engagement, thus securing knife 1544 with knife assembly 1540.

Figure 16:
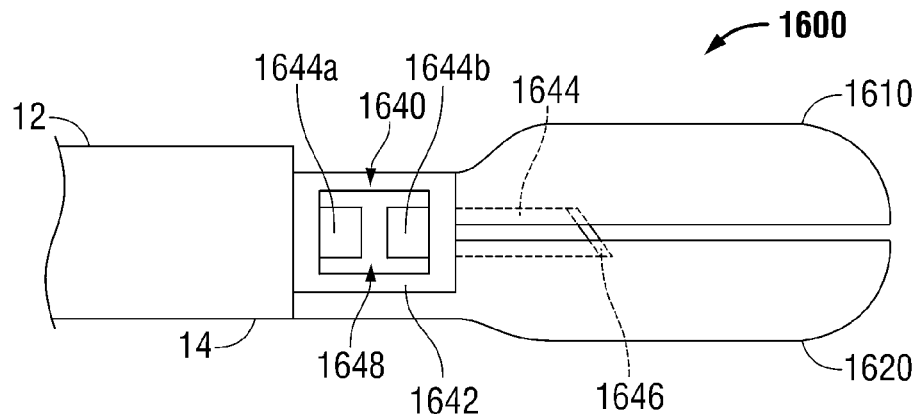
FIG. 16 is a side view of still another knife assembly provided in accordance with the present disclosure.

Referring now to FIG. 16, another embodiment of an end effector assembly is shown designated by reference numeral 1600. End effector assembly 1600 is disposed at distal end 14 of shaft 12 and generally includes first and second jaw members 1610, 1620 movable relative to one another between a spaced-apart position and an approximated position for grasping tissue therebetween. A knife assembly 1640 is disposed at least partially within shaft 12 and extends distally therefrom. Knife assembly 1640 includes a base portion 1642 that extends distally from shaft 12 and has a side, or lateral window 1648 defined therethrough. Knife assembly 1640 further includes a knife 1644 including a cutting blade 1646 defined at the distal end thereof. Knife 1644 is selectively translatable from a retracted position, wherein cutting blade 1646 is positioned proximally of jaw members 1610, 1620, and an extended position, as shown in FIG. 16, wherein knife 1644 extends between jaw members 1610, 1620 to cut tissue grasped therebetween.

With continued reference to FIG. 16, knife 1644 extends through base portion 1642 at least when knife 1644 is disposed in the extended position, such that knife 1644 is accessible through window 1648 at least in the extended position. Such a configuration allows the user to access knife 1644 through window 1648 for replacing knife 1644, or components thereof, without the need to disassemble end effector assembly 1600.

For example, at the completion of a surgical procedure, knife 1644 may be broken, or snapped into two components, a proximal component 1644a and a distal component 1644b. The breaking of knife 1644 may be accomplished using an instrument (not shown) inserted through window 1648, or in any other suitable manner. Knife 1644 may be formed from suitable material such that a clean break is achieved, i.e., such that no shattering or splintering occurs. Distal component 1644b may then be removed and discarded, or sterilized and prepared for re-use. The remainder of end effector assembly 1600 may similarly be prepped for re-use. Next, a second distal component 1644b (either a new distal component or the refurbished original distal component) is inserted into end effector assembly 1600 such that the ends of proximal and distal components 1644a, 1644b, respectively, are disposed in close proximity to one another. Thereafter, by positioning a welding instrument (not shown) adjacent window 1648, proximal and distal components 1644a, 1644b may be laser-welded, or otherwise secured to one another, once again forming a complete knife 1644 that is ready for re-use.

Various other configurations of knives and/or methods for engaging, disengaging, and replacing knives or the components thereof will be described in detail below. It is envisioned that any of these various configurations described with reference to FIGS. 17-22 may be used in conjunction with knife assembly 1640 and window 1648 to facilitate engaging, disengaging and replacing the knife or components thereof without substantially disrupting any of the other components of end effector assembly 1600.

Figure 17:
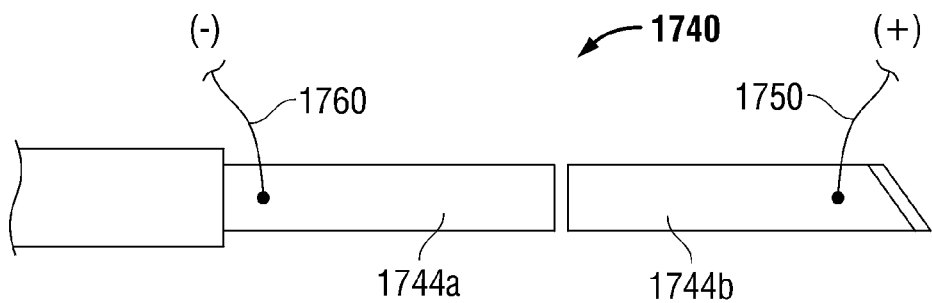
FIG. 17 is a side view of yet another knife assembly provided in accordance with the present disclosure.

Referring now to FIG. 17, in some embodiments, the proximal and distal components 1744a, 1744b, respectively, of the knife assembly 1740 may be welded to one another by positioning the ends of proximal and distal components 1744a, 1744b, respectively, in close proximity to one another and creating a potential difference therebetween, e.g., by coupling active and return leads 1750, 1760 thereto. As energy passes between the components 1744a, 1744b, the ends thereof are heated such that, ultimately, the proximal and distal components 1744a, 1744b may be welded to one another. Such a configuration is advantageous in that, the potentials may be provided by a generator (not shown), which is often used in conjunction with surgical forceps for providing energy to the jaw members thereof. In other words, no additional equipment, except for lead wires 1750, 1760, is required.

Figure 18:
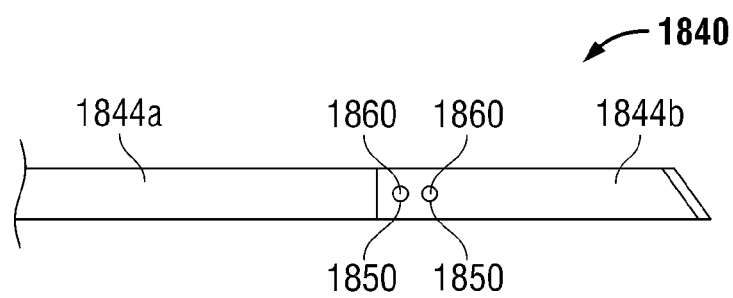
FIG. 18 is a side view of another knife assembly provided in accordance with the present disclosure.

FIG. 18 shows a configuration wherein the proximal and distal components 1844a, 1844b, respectively, of the knife assembly 1840 are pinned to one another via a pair of pin-aperture connections. More specifically, each of the components 1844a, 1844b includes a pair of apertures 1850 defined therethrough. Upon alignment of the apertures 1850 with one another, i.e., upon positioning of proximal and distal components 1844a, 1844b, respectively, adjacent one another, pins 1860 may be inserted through each aligned pair of apertures 1850 to releasably secure proximal and distal components 1844a, 1844b to one another. Alternatively, either or both of proximal and distal components 1844a, 1844b may include a post, while the other component 1844a, 1844b includes an aperture to achieve a post-aperture engagement therebetween.

Figure 19:
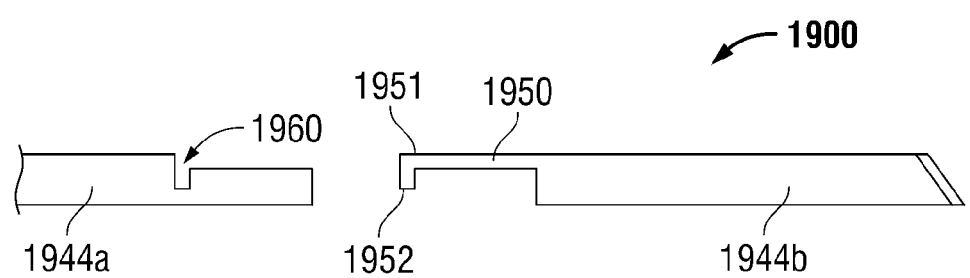
FIG. 19 is a side view of still yet another knife assembly provided in accordance with the present disclosure.
Figure 20:
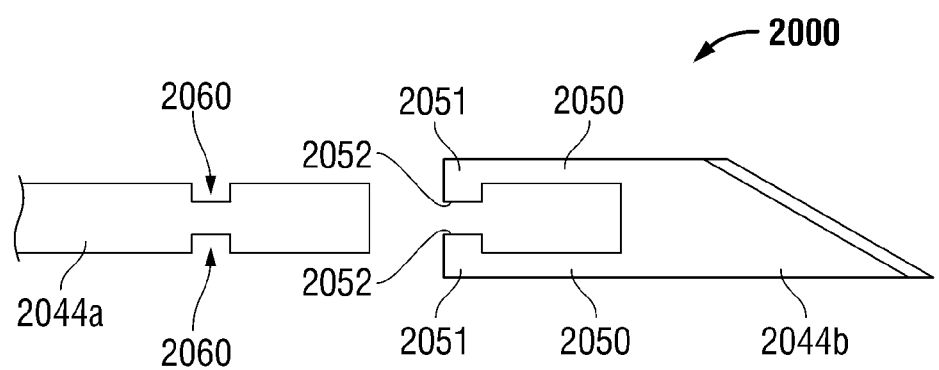
FIG. 20 is a side view of another knife assembly provided in accordance with the present disclosure.

With reference to FIGS. 19-20, one of the components of knife assemblies 1900, 2000, e.g., distal components 1944b, 2044b, may include one or more cantilever springs 1950, 2050 extending therefrom that each include a locking tab 1952, 2052 disposed at free end 1951, 2051 thereof. The other component, e.g., proximal component 1944a, 2044a, includes one or more notches 1960, 2060 defined therein that are shaped complementary to locking tab(s) 1952, 2052 such that locking tab(s) 1952, 2052 are resiliently and releasably engagable, e.g., snap-fit into engagement, within notch(es) 1960, 2060 to retain proximal and distal components 1944a, 1944b and 2044a, 2044b, respectively, in engagement with one another under the bias of cantilever spring(s) 1950, 2050.

Figure 21:
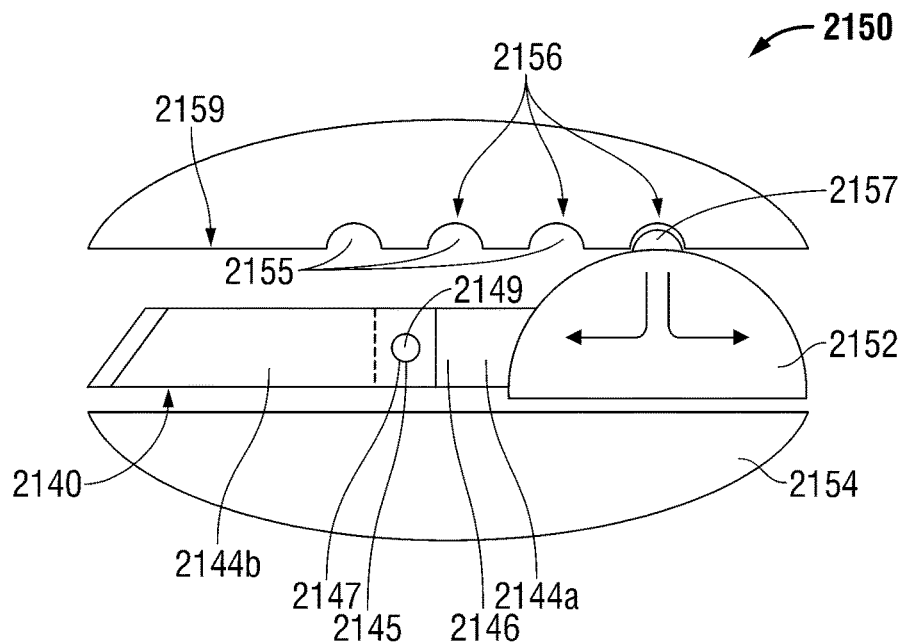
FIG. 21 is a side view of a releasable locking mechanism configured for use with a knife assembly provided in accordance with the present disclosure.

Turning to FIG. 21, a releasable locking mechanism for securing first and second components 2144a, 2144b of knife assembly 2140 to one another is shown generally identified by reference numeral 2150. Locking mechanism 2150 includes a knife holder 2152 that includes first component 2144a of knife assembly 2140 fixedly engaged thereon and extending therefrom. Knife holder 2152 is selectively translatable through housing 2154 of locking mechanism 2150 and is engagable therewith at a plurality of discrete locking positions 2156. More specifically, knife holder 2152 includes a protrusion 2157 extending therefrom that is biased upwardly, e.g., via a spring (not shown), into engagement within one of the recesses 2155 corresponding to each of the discrete locking positions 2156 of locking mechanism 2150. Knife holder 2152 is selectively depressible against the bias of the spring (not shown) such that knife holder 2152 can be slid along housing 2154 for locking engagement of protrusion 2157 within other recesses 2155 defined within housing 2154 and/or for positioning knife holder 2152 to permit engagement or disengagement of first and second components 2144a, 2144b, respectively, to one another.

As mentioned above, first component 2144a extends from knife holder 2152. More specifically, first component 2144a includes an aperture 2145 defined therethrough at free end 2146 thereof. Second component 2144b similarly includes an aperture 2147 defined at an end thereof for alignment with aperture 2145 of first component 2144a. Apertures 2145, 2147, when aligned with one another, are configured to receive a pin 2149 therethrough for securing first and second components 2144a, 2144b, respectively, to one another.

In order to engage and/or disengage first and second components 2144a, 2144b, respectively, to one another, knife holder 2152 is moved relative to housing 2154 to a fully extended, or unlocked position, wherein first component 2144a extends from housing 2154 and wherein protrusion 2157 of knife holder 2152 is disposed adjacent substantially linear segment 2159 of housing 2154. In this unlocked position, with first component 2144a extending from housing 2154, apertures 2145, 2147 of first and second components 2144a, 2144b, respectively, may be aligned with one another and pin 2149 may be inserted therethrough (or removed therefrom) to engage (or disengage) first and second components 2144a, 2144b to one another. Once engaged to one another, knife holder 2152 may be translated back until protrusion 2157 of knife holder 2152 is biased into engagement within one of recesses 2155 in the locked position. In the locked position, with apertures 2145, 2146 and pin 2149 disposed within housing 2154, disengagement therebetween is substantially inhibited. Further, knife 2144 is retained in position relative to housing under the biased engagement of protrusion 2157 of knife holder 2152 within one of recesses 2155 of housing 2154. The particular recesses 2155 within which protrusion 2157 is engaged may be selected in accordance with the desired distance that knife 2144 extends from housing 2154 which, ultimately, may depend on the configuration of the surgical instrument within which knife assembly 2140 is used and/or the particular surgical task to be performed.

As can be appreciated, the above-described configuration of knife assembly 2140 and releasable locking mechanism 2150 provides for simplified engagement and disengagement of first and second components 2144a, 2144b, respectively to one another. It is envisioned that releasable locking mechanism 2150 may be incorporated within shaft 12 (FIGS. 14A-14C), may extend from shaft 12 similar to base portion 1642 (FIG. 16) of end effector assembly 1600 (FIG. 16), may be disposed within base portion 1642 (FIG. 16) and accessible through window 1648 (FIG. 16), or may otherwise be configured to facilitate engagement and disengagement of first and second components 2144a, 2144b of knife assembly 2140 to one another.

Figure 22:
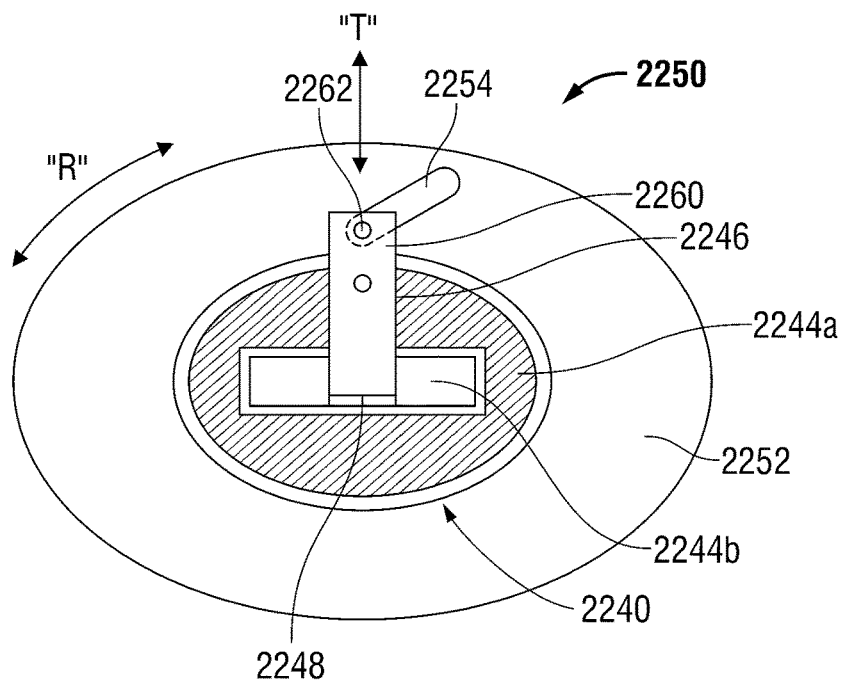
FIG. 22 is a transverse, cross-sectional view of a releasable locking mechanism configured for use with a knife assembly provided in accordance with the present disclosure.

Referring now to FIG. 22, another embodiment of a releasable locking mechanism for securing first and second components 2244a, 2244b of knife assembly 2240 to one another is shown generally identified by reference numeral 2250. Locking mechanism 2250 includes an outer sleeve 2252 disposed about first and second components 2244a, 2244b, respectively. More specifically, outer sleeve 2252 is disposed about first component 2244a, which, in turn, is disposed about at least a portion of second component 2244b. Outer sleeve 2252 includes a pin track 2254 defined therein and is selectively rotatable, as indicated by arrows "R," about first and second components 2244a, 2244b, respectively.

A locking tab 2260 is slidably positioned within a slot 2246 defined within first component 2244a and includes a pin 2262 extending therefrom that is engaged within pin track 2254 of outer sleeve 2252. Second component 2244b includes an aperture 2248 defined therein that is configured to receive locking tab 2260 therein to releasably engage first and second components 2244a, 2244b, respectively, to one another. More specifically, as outer sleeve 2252 is rotated relative to first and second components 2244a, 2244b, respectively, the configuration of pin track 2254 urges pin 2262 and, thus locking tab 2260 to translate through slot 2246, as indicated by arrows "T." Thus, outer sleeve 2252 is rotatable between an unlocked position, wherein locking tab 2260 is spaced-apart from second component 2244b such that second component 2244b may be removed from engagement with first component 2244a, and a locked position, wherein locking tab 2260 is translated into engagement with aperture 2248 define within second component 2244b such that first and second components 2244a, 2244b are secured to one another. As can be appreciated, such a configuration provides for simplified engagement and disengagement of first and second components 2244a, 2244b, respectively to one another. Further, outer sleeve 2252 may comprise a portion of the shaft 12 (FIGS. 14A-14C), may extend distally from shaft 12 similar to base portion 1642 (FIG. 16) of end effector assembly 1600 (FIG. 16), may be disposed within base portion 1642 (FIG. 16) and accessible through window 1648 (FIG. 16), or may otherwise be configured to facilitate engagement and disengagement of first and second components 2244a, 2244b of knife assembly 2240 to one another.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    first and second jaw members, each jaw member including a flexible proximal support arm defining an outer surface and a proximal end portion, and a distal portion defining an inner surface and extending from the respective flexible proximal support arm thereof, the distal portions of the jaw members disposed in parallel orientation relative to one another;
    a base member coupling the proximal end portions of the flexible proximal support arms to one another;
    a tube slidably disposed about at least a portion of the flexible proximal support arms of the first and second jaw members; and
    first and second rollers disposed within and rotatably coupled to the tube, the first roller disposed adjacent the flexible proximal support arm of the first jaw member in contact with the outer surface thereof, the second roller disposed adjacent the flexible proximal support arm of the second jaw member in contact with the outer surface thereof,
    wherein the tube is slidable about and relative to the first and second jaw members from a retracted position to an extended position, the first and second rollers rolling along the outer surfaces of the flexible proximal support arms of the respective jaw members upon movement of the tube from the retracted position to the extended position to move the inner surfaces of the distal portions of the first and second jaw members from a spaced-apart position to an approximated position for grasping tissue therebetween, while maintaining the distal portions of the jaw members in parallel orientation relative to one another.

2. The forceps according to claim 1, wherein upon movement of the tube from the retracted position to the extended position the first and second rollers roll along the outer surfaces of the flexible proximal support arms of the respective jaw members to flex the flexible proximal support arms of the first and second jaw members to move the inner surfaces of the distal portions of the first and second jaw members from the spaced-apart position to the approximated position.

3. The forceps according to claim 1, wherein the inner surfaces of the distal portions of the first and second jaw members are electrically-conductive and configured to conduct energy through tissue grasped therebetween to treat tissue.

4. The forceps according to claim 1, further including a rod coupled to and extending proximally from the base member through the tube.

5. The forceps according to claim 4, wherein the base member is releasably engagable with the rod to enable replacement of the first and second jaw members.

6. The forceps according to claim 4, further including a shaft disposed about the tube, wherein the shaft and the rod are longitudinally stationary relative to one another.

7. A forceps, comprising:
    a housing;
    a shaft engaged to and extending distally from the housing;
    a rod disposed within the shaft and longitudinally fixed relative to the shaft;
    first and second jaw members extending distally from the rod, each jaw member including a flexible proximal support arm defining an outer surface and a proximal end portion, and a distal portion defining an inner surface and extending from the respective flexible proximal support arm thereof, the distal portions of the jaw members disposed in parallel orientation relative to one another;
    a base member extending distally from the rod, wherein the base member couples the proximal end portions of the flexible proximal support arms to one another;
    a tube slidably disposed within the shaft and about the rod; and
    first and second rollers disposed within and rotatably coupled to the tube, the first roller disposed adjacent the flexible proximal support arm of the first jaw member in contact with the outer surface thereof, the second roller disposed adjacent the flexible proximal support arm of the second jaw member in contact with the outer surface thereof,
    wherein the tube is slidable about and relative to the first and second jaw members from a retracted position to an extended position, the first and second rollers rolling along the outer surfaces of the flexible proximal support arms of the respective jaw members upon movement of the tube from the retracted position to the extended position to move the inner surfaces of the distal portions of the first and second jaw members from a spaced-apart position to an approximated position for grasping tissue therebetween, while maintaining the distal portions of the jaw members in parallel orientation relative to one another.

8. The forceps according to claim 7, further including a handle assembly extending from the housing and operably coupled to the tube, the handle assembly including a movable handle selectively movable between a first position and a second position for moving the tube between the retracted position and the extended position.

9. The forceps according to claim 7, wherein upon movement of the tube from the retracted position to the extended position the first and second rollers roll along the outer surfaces of the flexible proximal support arms of the respective jaw members to flex the flexible proximal support arms of the first and second jaw members to move the inner surfaces of the distal portions of the first and second jaw members from the spaced-apart position to the approximated position.

10. The forceps according to claim 7, wherein the inner surfaces of the distal portions of the first and second jaw members are electrically-conductive and configured to conduct energy through tissue grasped therebetween to treat tissue.

11. The forceps according to claim 7, wherein the base member is configured to releasably couple to the rod to enable replacement of the first and second jaw members.

* * * * *